(12) United States Patent
Martin

(10) Patent No.: US 10,966,979 B2
(45) Date of Patent: Apr. 6, 2021

(54) AMORPHOUS SOLID DISPERSION OF AN ORALLY AVAILABLE GONADOTROPIN-RELEASING HORMONE RECEPTOR ANTAGONIST

(71) Applicant: Sandoz AG, Basel (CH)

(72) Inventor: Nolwenn Martin, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 16/498,525

(22) PCT Filed: Apr. 11, 2018

(86) PCT No.: PCT/EP2018/059219
§ 371 (c)(1),
(2) Date: Sep. 27, 2019

(87) PCT Pub. No.: WO2018/189213
PCT Pub. Date: Oct. 18, 2018

(65) Prior Publication Data
US 2020/0022980 A1    Jan. 23, 2020

(30) Foreign Application Priority Data
Apr. 13, 2017 (EP) .................... 17166537

(51) Int. Cl.
*A61K 31/513* (2006.01)
*A61K 9/10* (2006.01)
*A61K 47/02* (2006.01)

(52) U.S. Cl.
CPC .......... *A61K 31/513* (2013.01); *A61K 9/10* (2013.01); *A61K 47/02* (2013.01)

(58) Field of Classification Search
CPC .................................................. A61K 31/513

USPC ......................................................... 414/274
See application file for complete search history.

(56) References Cited

U.S. PATENT DOCUMENTS

2019/0321363 A1* 10/2019 Peddireddy ............ A61K 9/143

FOREIGN PATENT DOCUMENTS

| WO | 2005007165 A1 | 1/2005 |
| WO | 2009062087 A1 | 5/2009 |
| WO | 2017007895 A1 | 1/2017 |

OTHER PUBLICATIONS

Chen, Journal of Medicinal Chemistry (2008), 51(23), 7478-7485.*
Kumar, International Journal of Pharmaceutics 461 (2014) 459-468.*
Chen, Chen, et al., J. Med. Chem., 2008, vol. 51, No. 23, pp. 7478-7485.
International Search Report and Written Opinion for PCT/EP2018/059219, dated Oct. 18, 2018, 11 pages.
Pecharsky, et al., Fundamentals of Powder Diffraction and Structural Characterization of Materials, Springer, 2005, p. 3.

* cited by examiner

*Primary Examiner* — Nizal S Chandrakumar
(74) *Attorney, Agent, or Firm* — Luedeka Neely Group, P.C.

(57) ABSTRACT

The invention relates to an amorphous solid dispersion comprising elagolix sodium and at least one silicon-based inorganic compound and to a process for preparing the same. Furthermore, it relates to a pharmaceutical composition comprising said solid dispersion and one or more additional pharmaceutical acceptable excipient(s), wherein the pharmaceutical composition can be used as a medicament, in particular for the treatment of endometriosis and uterine fibroids.

7 Claims, 2 Drawing Sheets

AMORPHOUS SOLID DISPERSION OF AN ORALLY AVAILABLE GONADOTROPIN-RELEASING HORMONE RECEPTOR ANTAGONIST

This application is a Section 371 national phase entry of PCT application PCT/EP2018/059219, filed Apr. 11, 2018. This application also claims the benefit of the earlier filing date of European patent application 17166537.5, filed Apr. 13, 2017.

FIELD OF THE INVENTION

The invention relates to an amorphous solid dispersion comprising elagolix sodium and at least one silicon-based inorganic compound and to a process for preparing the same. Furthermore, it relates to a pharmaceutical composition comprising said solid dispersion and one or more pharmaceutical acceptable excipient(s), wherein the pharmaceutical composition can be used as a medicament, in particular for the treatment of endometriosis and uterine fibroids.

BACKGROUND OF THE INVENTION

Elagolix is an orally available gonadotropin-releasing hormone (GnRH) receptor antagonist currently under investigation in clinical phase III trials for the treatment of endometriosis and uterine fibroids. The chemical name of elagolix is 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenylethyl]amino]butanoic acid. Elagolix is an uracil derivative, which can be represented by the chemical structure according to Formula (I)

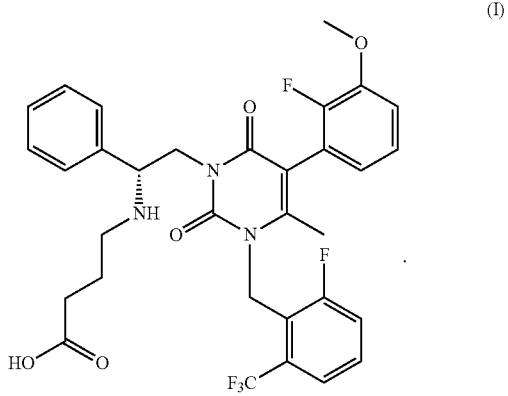 [SMILES: COc1cccc(-c2c(C)n(Cc3c(F)cccc3C(F)(F)F)c(=O)n(C[C@H](NCCCC(=O)O)c3ccccc3)c2=O)c1F]

(I)

WO 2005/007165 A1 discloses pyrimidine-2,4-dione derivatives as gonadotropin-releasing hormone receptor antagonists. The compound elagolix is disclosed as one example of such pyrimidine-2,4-dione derivatives. In Example 1H of said application elagolix free acid was formed as an intermediate during production of the elagolix sodium salt and was described as a white gel after extraction with ethyl acetate and evaporation of the solvent. The gel was passed through a DOWEX MSC-1 macroporous strong cation-exchange column to convert the acid to the sodium salt. Finally, lyophilization gave the sodium salt of elagolix as a white solid.

According to Chen C. et al. "Discovery of Sodium R-(+)-4-{2-[5-(2-Fluoro-3-methoxyphenyl)-3-(2-fluoro-6-[trifluoromethyl]benzyl)-4-methyl-2,6-dioxo-3,6-dihydro-2H-pyrimidin-1-yl]-1-phenylethylamino}butyrate (Elagolix), a Potent and Orally Available Nonpeptide Antagonist of the Human Gonadotropin-Releasing Hormone Receptor" J. Med. Chem., 2008, 51 (23), 7478-7485 elagolix free acid was either obtained as white foam or as gel after extraction with ethyl acetate and subsequent evaporation of the solvent. As already previously described in WO 2005/007165 A1 the gel was passed through a DOWEX MSC-1 macroporous strong cation-exchange column to convert it to the sodium salt, which was obtained as white solid after lyophilization.

WO 2009/062087 A1 describes processes for the preparation of uracil derivatives, a class of gonadotropin-releasing hormone receptor antagonists including elagolix. Elagolix free acid (Example 4, final product of step 4B) and its sodium salt (Example 5, final product of step 5B and alternate step 5B) were both obtained as off-white solids. On page 6, the application describes the compounds of the application as amorphous solids and goes on to suggest that the compounds of the application are formulated as amorphous cosolutions, for example by spray-drying with excipients such as PVP (polyvinyl pyrrolidone, Kollidons) or HPMC (hydroxypropylmethylcellulose). Amorphous elagolix sodium is described as preferred for that purpose and in Example 9 a solid amorphous mixture was prepared from elagolix sodium and polymers such as HPMC and Kollidon, wherein an excess of polymer at a weight ratio of 1:3 has been used.

The drug substance elagolix is described to be an amorphous hygroscopic solid on page 10 of WO 2017/007895 A1. In Examples 1 and 2 of said application, elagolix drug substance was employed in form of its sodium salt.

It is noteworthy that elagolix sodium is highly hygroscopic and was found to even deliquesce upon moisture contact. Said properties require special care and precautionary measures such as a controlled atmosphere during pharmaceutical processing, which renders manufacturing cumbersome and expensive. Furthermore, the solid dispersions of elagolix sodium with HPMC and Kollidons, which are disclosed in WO 2009/062087 A1 introduce the 3-fold amount of polymers in relation to the active substance, which significantly increases the weight and therefore also the volume of an oral solid dosage form such as a tablet or a capsule. Such formulations may negatively influence patients' compliance, in particular for elderly people having troubles swallowing.

It was thus an objective of the present invention to provide improved solid forms of elagolix sodium, which do not deliquesce upon moisture contact and which do not require large amounts of excipients in order to achieve said effect and therefore may improve patients' compliance.

SUMMARY OF THE INVENTION

The present invention provides a solid dispersion comprising amorphous elagolix sodium and at least one silicon-based inorganic compound. It was found that the solid dispersion of the present invention does not require an excess of excipients over elagolix in order to prevent elagolix sodium from deliquescence upon moisture contact. For example, a 1:1 weight ratio of elagolix sodium and a silica-based inorganic compound is sufficient to prevent deliquescence of elagolix sodium. Hence, the solid dispersion of the present invention is advantageous for the use in the pharmaceutical field, in particular for storage and/or for the preparation of a pharmaceutical composition.

Abbreviations
PXRD powder X-ray diffractogram
RH relative humidity
RT room temperature Definitions In the context of the present invention the following definitions have the indicated meaning, unless explicitly stated otherwise:

The term "elagolix" as used herein refers to the compound with the chemical name 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenylethyl]amino]butanoic acid, which is represented by the chemical structure as depicted in Formula (I) of the present invention. In the present invention "elagolix" indicates the free acid form, where the hydrogen atom of the carboxylic acid group is not substituted by another kind of atom, for example by sodium or potassium.

As used herein, the term "elagolix sodium" herein refers to the sodium salt of the compound with the chemical name 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenylethyl]amino]butanoic acid, which is represented by the chemical structure as depicted in Formula (II) of the present invention. In the present invention "elagolix sodium" indicates that the hydrogen atom of the carboxylic acid group is substituted by sodium.

As used herein, the term "silicate" refers to naturally occurring or synthesized compounds containing an anionic silicon compound, preferably an oxide.

The term "silica" as used herein refers to silicon dioxide in its various forms, such as naturally occurring or synthesized silica.

As used herein the term "silicon-based inorganic adsorbent" refers to a silicon-based inorganic compound having a high porosity and a large surface area which allows at least some adsorption of amorphous elagolix sodium to it. The "silicon based inorganic adsorbent" is an inert material with a sufficiently high BET specific surface area of at least 1 $m^2/g$. Preferably, the BET specific surface area is at least 10 $m^2/g$, such as from 10 $m^2/g$ to 1000 $m^2/g$, for example from 20 $m^2/g$ to 500 $m^2/g$.

As used herein the term "room temperature" refers to a temperature in the range of from 20 to 30° C., preferably to a temperature in the range of from 22 to 27° C., more preferably to a temperature in the range of from 23 to 26° C.

As used herein the term "amorphous" refers to a solid compound or a mixture of solid compounds that is/are not crystalline. An amorphous compound or a mixture of amorphous compounds possess(es) no long-range order but only display(s) short-range order and hence do(es) not display a definitive X-ray diffraction pattern with reflections but only result in broad scattering. According to literature, long-range order e.g. extends over approximately 103 to 1020 atoms, whereas short-range order is over a few atoms only (see "*Fundamentals of Powder Diffraction and Structural Characterization of Materials*" by Vitalij K. Pecharsky and Peter Y. Zavalij, Kluwer Academic Publishers, 2003, page 3).

The term "reflection" with regards to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order.

As used herein, the term "measured at a temperature in the range of from 20 to 30° C." refers to a measurement under standard conditions. Typically, standard conditions mean a temperature in the range of from 20 to 30° C., i.e. at room temperature. A preferred temperature for measurements is 22° C. Typically, standard conditions additionally mean a measurement at 20% to 75% RH, with about 40% RH being a preferred controlled humidity value for a measurement.

A solid dispersion comprising amorphous elagolix sodium and at least one silicon-based inorganic compound may be referred herein as being characterized by graphical data "as shown in" a figure. Such data include, for example, powder X-ray diffractograms. The person skilled in the art understands that factors such as variations in instrument type, response and variations in sample directionality, sample concentration and sample purity may lead to small variations for such data when presented in graphical form.

A "predetermined amount" as used herein with regard to a solid dispersion comprising amorphous elagolix sodium and at least one silicon-based inorganic compound refers to a defined amount of said solid dispersion to be used for the preparation of a unit dose of a pharmaceutical composition.

The term "effective amount" as used herein with regard to a solid dispersion comprising amorphous elagolix sodium and at least one silicon-based inorganic compound encompasses an amount of said solid dispersion, which causes a desired therapeutic and/or prophylactic effect.

As solid dispersion comprising amorphous elagolix sodium and at least one silicon-based inorganic compound may be referred herein as being characterized by graphical data "as shown in" a figure. Such data include, for example, powder X-ray diffractograms. The person skilled in the art understands that factors such as variations in instrument type, response and variations in sample directionality, sample concentration and sample purity may lead to small variations for such data when presented in graphical form.

As used herein the term "deliquescent" means the property of a solid form of a compound to readily absorb moisture form the surrounding atmosphere until it deliquesces and forms a solution upon storage for 14 days at 40° C., atmospheric pressure and 75% relative humidity.

DETAILED DESCRIPTION OF THE INVENTION

Figure 1:
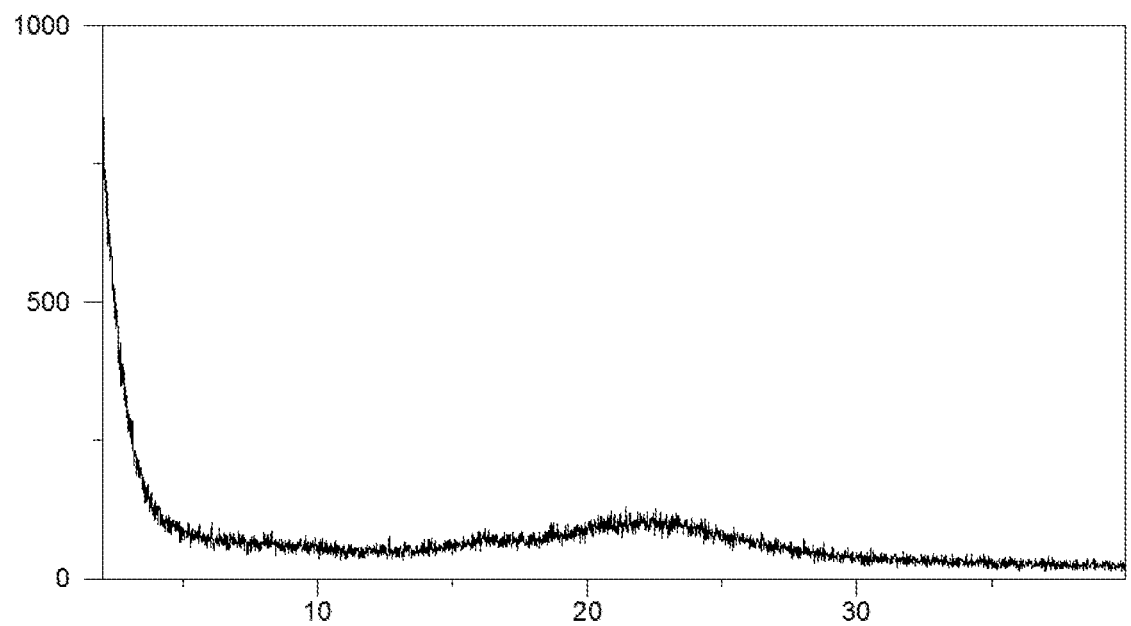
FIG. 1: illustrates a representative powder X-ray diffractogram of the solid dispersion comprising amorphous elagolix sodium and Syloid® 72P prepared according to Example 1.1 of the present invention. The x-axis shows the scattering angle in °2-Theta, the y-axis shows the intensity of the scattered X-ray beam in counts of detected photons.

The present invention relates to a solid dispersion comprising amorphous elagolix sodium and at least one silicon-based inorganic compound, preferably one silicon-based inorganic compound having a BET specific surface area of at least 1 m$^2$/g.

Elagolix sodium can be represented by the chemical structure as depicted in Formula (II)

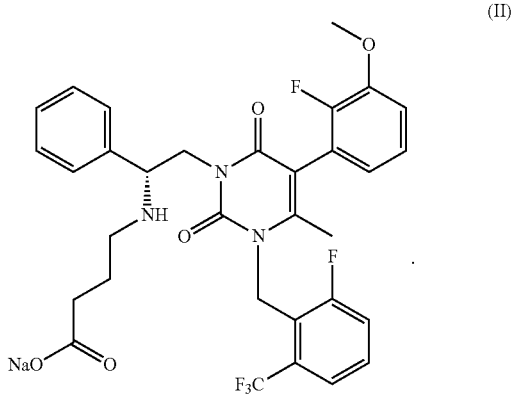

(II)

The silicon-based inorganic compound is preferably a silicon-based inorganic adsorbent, i.e. a silicon-based inorganic compound having a high porosity and a large surface area that enable it to adsorb elagolix sodium to it. The "silicon based inorganic adsorbent" is preferably a material with a high BET specific surface area of at least 1 m$^2$/g. Preferably, the BET specific surface area is at least 10 m$^2$/g, such as from 10 m$^2$/g to 1000 m$^2$/g, for example from 20 m$^2$/g to 500 m$^2$/g. Preferred silicon-based inorganic adsorbents are silica, silicates, and combinations of one or more silica with one or more silicate(s).

In one aspect, the silicon-based inorganic compound is silica. The silica is preferably selected from the group consisting of fumed silica, precipitated silica, gel silica, colloidal silica, and a combination of two or more thereof, such as a combination of fumed silica and precipitated silica or a combination of fumed silica and colloidal silica or a combination of fumed silica and gel silica or a combination of precipitated silica and gel silica or a combination of precipitated silica and colloidal silica or a combination of gel silica and colloidal silica or a combination of fumed silica and precipitated silica and gel silica or a combination of fumed silica and gel silica and colloidal silica or a combination of precipitated silica and gel silica and colloidal silica or a combination of fumed silica and precipitated silica and gel silica and colloidal silica. Preferred silica include, but are not restricted to, the commercially available compounds Syloid® 72 FP, Syloid® 244 FP and Syloid® AL-1 FP, all from Grace.

In another aspect, the silicon-based compound is a silicate. The silicate is preferably an aluminosilicate or an aluminometasilicate which, more preferably, additionally contains at least one alkali metal element selected from the group consisting of Li, Na, K, Rb, Cs and a combination of two or more thereof, preferably from the group consisting of Li, Na, K, and a combination of two or more thereof, more preferably from the group consisting of Na, K, and a combination of two or more thereof, and/or at least one alkaline earth metal element selected from the group consisting of Mg, Ca, Sr, Ba, and a combination of two or more thereof, preferably from the group consisting of Mg, Ca, Ba, and a combination of two or more thereof, preferably from the group consisting of Mg, Ca, and a combination of two or more thereof. More preferably, the silicate is an aluminosilicate or an aluminometasilicate which additionally contains at least one alkaline earth metal element selected from the group consisting of Mg, Ca, Sr, Ba, and a combination of two or more thereof, preferably from the group consisting of Mg, Ca, Ba, and a combination of two or more thereof, preferably from the group consisting of Mg, Ca, and a combination of two or more thereof. More preferably, the silicate is an aluminometasilicate, which additionally contains Mg. Preferred magnesium aluminometasilicate include, but are not restricted to, the commercially available compounds Neusilin® UFL2, Neusilin® US2, both from Fuji Chemical Industry Co., Ltd.

Examples of silicates include, but are not restricted to, nesosilicates comprising the structure unit $[SiO_4]_4$-, sorosilicates comprising the structure unit $[Si_2O_7]_6$-, cyclosilicates comprising the structure unit $[Si_nO_{3n}]_{2n}$-, single chain inosilicates comprising the structure unit $[Si_nO_{3n}]_{2n}$-, double chain inosilicates comprising the structure unit $[Si_{4n}O_{11n}]_{6n}$-, phyllosilicates comprising the structure unit $[Si_nO_{5n}]_{2n}$-, or tectosilicates with a 3D framework comprising the structure unit $[Al_xSi_yO_{2(x+y)}]_x$-.

Silicon-based inorganic compounds have preferably a pH in a defined range, preferably a pH of at least 5.0 as determined using a pH meter in a solution of 400 mg of the silicon-based inorganic compound in 10 mL of de-ionized water at 25° C. More preferably, the at least one silicon-based compound has a pH in the range of from 5.0 to 9.0, more preferably in the range of from 5.3 to 8.5, more preferably in the range of from 5.5 to 8.0.

Generally, it is conceivable that the solid dispersion of the present invention contains at least one silicon-based inorganic compound having a pH in the above-defined preferred ranges and at least one silicon-based inorganic compound having a pH outside these ranges. Preferably, all silicon-based inorganic compounds comprised in the solid composition of the present invention have a pH in the above-defined preferred ranges.

Preferably, the bulk density of the silicon-based inorganic compound is in the range of from 10 to 700 g/L, preferably in the range of from 30 to 650 g/L, more preferably in the range of from 50 to 600 g/L. Bulk density as used herein is defined as tapped bulk density determined according to Method A on page 4 of the WHO document QAS/11.450 FINAL from March 2012, with the heading "S.3.6. BULK DENSITY AND TAPPED DENSITY OF POWDERS". Generally, it is conceivable that the solid dispersion of the present invention contains at least one silicon-based inorganic compound having a bulk density in the above-defined preferred ranges and at least one silicon-based inorganic compound having a bulk density outside these ranges. Preferably, all silicon-based inorganic compound comprised in the solid composition of the present invention have a bulk density in the above-defined preferred ranges.

Generally, the silica and/or the silicate can be present in crystalline or amorphous form. Preferably, at least 90 weight-%, more preferably at least 95 weight-%, more preferably at least 99 weight-% of the at least one silicon-based inorganic compound are present in amorphous form. More preferably, at least 99.5 weight-%, more preferably at least 99.9 weight-%, more preferably at least 99.99 weight-% of the at least one silicon-based inorganic compound are present in amorphous form.

The weight ratio of elagolix sodium and the at least one silicon-based inorganic compound is preferably in the range of from 1.0:0.1 to 1.0:1.5, more preferably of from 1.0:0.2 to 1.0:1.2, for example the weight ratio is 1.0:1.0. The weight ratio is calculated based on the total amount of elagolix sodium present in said solid dispersion and based on the total amount of the at least one silicon-based inorganic compound present in said solid dispersion, i.e. if two or more silicon-based inorganic compounds are present in the solid dispersion of the present invention, the combined weight of these is taken for the calculation of the weight ratio.

Alternatively, the solid dispersion of the present invention comprises at least 40 weight-%, preferably at least 45 weight-%, more preferably at least 50 weight-% for example at least 70 weight-% or at least 80 weight-% and at most 95 weight-%, preferably at most 90 weight-% of amorphous elagolix sodium, based on the combined weight of the amorphous elagolix sodium and the at least one silicon-based inorganic compound.

In one embodiment, the solid dispersion comprising amorphous elagolix sodium and at least one silicon-based inorganic compound as defined above is characterized by a powder X-ray diffractogram comprising no reflection in the range of from 2 to 40° 2-Theta, when measured at a temperature in the range of from 20 to 30° C. with Cu-Kalpha$_{1,2}$ radiation having a wavelength of 0.15419 nm.

Preparation Process of the Solid Dispersion

The present invention also relates to a process for preparing the solid dispersion comprising amorphous elagolix sodium and at least one silicon-based inorganic compound as described above comprising the steps of:

(a) providing a mixture comprising elagolix sodium, at least one silicon-based inorganic compound and one or more solvent(s); and (b) removing at least a part of the one or more solvent(s) to provide the solid dispersion.

Elagolix sodium provided in step (a) can be prepared according to the teaching of WO 2009/062087 A1 Example 5 yielding amorphous material. The at least one silicon-based inorganic compound is preferably a silicon-based inorganic adsorbent, selected from the group consisting of silica, silicates, and a combination of two or more thereof as described above in detail.

The one or more solvent(s), which may be employed in step (a) is a solvent or solvent mixture in which elagolix sodium has an adequate solubility and the at least one silicon-based inorganic compound may be suitably dispersed. The term "adequate solubility" means a solubility at room temperature of greater than about 10 g/L. Preferred solvents are selected from the group consisting of water, acetonitrile, $C_3$-$C_5$ ketones, $C_1$-$C_2$ halogenated hydrocarbons, $C_3$-$C_4$ alcohols, $C_2$-$C_6$ ethers, $C_3$-$C_5$ esters, and a combination of two or more thereof. More preferably, the solvent comprises, and for example consists of, dichloromethane, chloroform, ethanol, methanol, tetrahydrofuran, 2-methyltetrahydrofuran, 2-propanol, 2-methyl-2-propanol, ethyl acetate, acetone, acetonitrile, water or mixtures of two or more thereof. Even more preferably, the solvent comprises, and for example consists of, dichloromethane, tetrahydrofuran, 2-methyltetrahydrofuran, acetone, acetonitrile, water or mixtures of two or more thereof. More preferably, the solvent comprises dichloromethane, acetone, acetonitrile, water or mixtures of two or more thereof. Most preferably the solvent comprises, more preferably the solvent is acetonitrile, water or a mixture of acetonitrile and water.

Elagolix sodium and the at least one silicon-based inorganic compound are dissolved or dispersed in one or more solvent(s), whereat the components may be dissolved or dispersed simultaneously or subsequently. Preferably, elagolix sodium is first dissolved in one or more solvent(s) and the at least one silicon-based compound is subsequently dispersed in the elagolix sodium solution. Consequently, solvents are preferred in which elagolix sodium can be dissolved and the at least one silicon-based inorganic compound can be dispersed.

Preferably, the elagolix sodium solution is prepared at a temperature in the range of from 10 to 30° C., more preferably in the range of from 20 to 25° C., preferably at ambient pressure. The obtained elagolix sodium solution may optionally be purified before the at least one silicon-based inorganic compound is added. The term "purified" in this context means that non-dissolved particles, such as impurities, may be removed by suitable methods known to those skilled in the art such as centrifugation, filtration, ultrafiltration or the like. Preferably, the at least one silicon-based inorganic compound is dispersed in the elagolix solution at a temperature in the range of from 10 to 30° C., more preferably in the range of from 20 to 25° C., preferably at ambient pressure.

Preferably, the weight ratio of elagolix sodium and the at least one silicon-based inorganic compound relative to the one or more solvent(s) applied is in the range of from 0.01:1.00 to 0.40:1.00, more preferably in the range of from 0.01:1.00 to 0.20:1.00. However, no specific restrictions exist regarding the weight ratio of elagolix sodium and the at least one silicon-based inorganic compound relative to the one or more solvent(s) applied, provided that the finally obtained mixture is a mixture, wherein the at least one silicon-based inorganic compound is dispersed in a solution of the elagolix sodium in the one or more applied solvent(s), which mixture can be subjected to the subsequent step (b).

In step (b) of the above-described process, at least a part, preferably essentially all, of the one or more solvent(s) is removed. "Essentially all" means that at least 95% by weight, more preferably at least 99% by weight, more preferably at least 99.9% by weight of the one or more solvent(s) present in the mixture according to step (a) is removed in step (b). Preferably, the solid dispersion obtained or obtainable by this process thus comprises less than 5% by weight, more preferably less than 1% by weight, more preferably less than 0.1% by weight of the one or more solvent(s), based on the total weight of the solid dispersion. Most preferably, all of the one or more solvent(s) present in the solution is removed to give the solid dispersion. The removal of the one or more solvent(s) may be carried out by any suitable method known to those skilled in the art such as evaporation, spray drying, lyophilization, melt extrusion, drum drying, or other solvent removal processes. Preferably, the one or more solvent(s) is/are removed by lyophilization, by spray drying or by vacuum drying or evaporation. Most preferably, the one or more solvent(s) is/are removed by lyophilization or by spray drying. Spray drying is a process well known to those skilled in the art for preparing solid dispersions. In such a spray drying process, the solution is pumped through an atomizer into a drying chamber thereby removing the solvent to form the solid dispersion. A drying process uses hot gases, such as air, nitrogen, nitrogen-enriched air or argon, to dry the particles. The solution can be atomized by conventional means well known in the art, such as a two-fluid sonication nozzle and a two-fluid non-sonication nozzle. If the solvent is removed by lyophilization, the sample temperature during lyophilization may be varied or held essentially constant and is preferably in the range of from 20 to 40° C., more preferably in the range of from 25 to 40° C.

In a further aspect of the present invention, step (a) of the above preparation process may further comprises the initial steps of:

(a1) providing a solution of elagolix in one or more solvent(s) and adding sodium hydroxide, (a2) optionally concentrating the solution obtained in (a1).

Elagolix provided in step (a1) can be prepared according to the teaching of WO 2009/062087 A1 Example 4 yielding amorphous material.

The one or more solvent(s) used in step (a1) may be the same or different from the one or more solvent(s) used in step (a) above. Preferably, the one or more solvent(s) used in step (a1) is/are the same as the one or more solvent(s) used in step (a). In step (a2) the term "concentrating the solution" means reducing the volume of the solution.

The invention also relates to a solid dispersion comprising amorphous elagolix and at least one silicon-based inorganic compound obtainable or obtained by the above described process.

Pharmaceutical Compositions and Use

In another aspect, the present invention relates to the use of the solid dispersion comprising amorphous elagolix sodium and at least one silicon-based inorganic compound as defined above for the preparation of a pharmaceutical composition.

In a further aspect, the present invention relates to a pharmaceutical composition comprising the solid dispersion comprising amorphous elagolix sodium and at least one silicon-based inorganic compound as defined above, preferably in a predetermined and/or effective amount and one or more pharmaceutically acceptable excipient(s).

In a preferred embodiment, the predetermined and/or effective amount the solid dispersion comprising amorphous elagolix sodium and at least one silicon-based inorganic compound is selected from the group consisting of 25 mg, 50 mg, 75 mg, 100 mg, 125 mg, 150 mg, 175 mg, 200 mg, 225 mg, 250 mg, 275 mg and 300 mg calculated as elagolix.

In a further preferred embodiment, the one or more pharmaceutically acceptable excipient(s) of the pharmaceutical composition as defined above is/are one or more diluent(s). Preferably, the one or more diluent(s) is/are selected from the group consisting of carbohydrates such as sugars, sugar alcohols, starches and celluloses. In another embodiment, the sugar may be selected from the group consisting of lactose, e.g. lactose monohydrate, anhydrous lactose or spray dried lactose, sucrose, dextrose, fructose, glucose, maltose and maltodextrin. In still another embodiment, the sugar alcohol may be selected from the group consisting of mannitol, sorbitol, xylitol and inositol. In a further embodiment the starches may be selected from corn starch and potato starch, whereas the starches are preferably pre-gelatinized or hydrolyzed. In yet another embodiment the celluloses may be selected from the group consisting of powdered cellulose, microcrystalline cellulose and silicified cellulose. In another preferred embodiment the one or more diluent(s) may also be selected from inorganic materials such as but not limited to calcium phosphate, calcium carbonate, calcium sulfate, calcium lactate, sodium chloride, magnesium oxide and magnesium carbonate.

In still another preferred embodiment, the pharmaceutical composition of the present invention is an oral solid dosage form such as a tablet or a capsule and most preferably the pharmaceutical composition is a tablet.

The pharmaceutical composition as defined above may be prepared by pharmaceutical standard procedures e.g. by wet or dry processing methods. In certain embodiments the pharmaceutical composition is prepared by wet processing methods, such as, but not limited to, wet granulation methods. Suitable wet granulation methods comprise high-shear granulation or fluid bed granulation. In another embodiment the pharmaceutical composition is prepared by dry processing methods, such as, but not limited to, direct compression or dry granulation methods. An example of dry granulation is roller compaction. The pharmaceutical composition obtained by dry or wet processing methods are preferably compressed into tablets or encapsulated.

The present invention also relates to the pharmaceutical composition as defined above for use as a medicament.

Finally, the invention relates to the pharmaceutical composition as defined above for the treatment of endometriosis and uterine fibroids.

Advantages

In contrast to neat amorphous elagolix sodium, which deliquesces fairly quickly upon moisture contact, the solid dispersion of the present invention comprising at least one silicon-based inorganic compound shows no deliquescence, e.g. when subjected to accelerated stress conditions of 40° C. and 75% RH (see also Example 2 herein). This is advantageous since there is no need for precautionary measures, which protects the solid dispersion of the present invention during drug product manufacturing from moisture and there is also no need for expensive packaging material, which protects the solid dispersion of the present invention or the final drug product comprising the same from humid atmospheres during storage.

Unexpectedly, it is not necessary to use an excess of the silicon-based inorganic compound over elagolix for the preparation of the solid dispersion of the present invention in order to prevent elagolix sodium from deliquescence. This is advantageous over the solid dispersions disclosed in WO 2009/062087 A1, where a 3-fold excess in terms of weight of polymers in relation to the weight of elagolix sodium was employed, which significantly increases the overall weight of the solid dispersion and therefore also the volume of an oral solid dosage form prepared from the solid dispersion, such as a tablet or a capsule. Such formulations may negatively influence patients' compliance, in particular for elderly people having troubles swallowing. Finally, the lower amount of silicon-based inorganic compounds used for the production of the solid dispersion of the present invention compared to the amount of polymers used for the production of the solid dispersions of WO 2009/062087 A1 also reduces raw material and production costs.

EXAMPLES

The following analytical method and parameters have been applied for the generation of the powder X-ray data disclosed in the present invention:

Powder X-Ray Diffraction

Powder X-ray diffraction was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-Theta with 40 s per step (255 channels) in the angular range of 2° to 40° 2-Theta at ambient conditions.

Example 1: Preparation of Amorphous Solid Dispersions Comprising Elagolix Sodium and at Least One Silicon-Based Inorganic Compound in a 1:1 Weight Ratio

Example 1.1: Amorphous Solid Dispersion of Elagolix Sodium With Syloid® 72FP Syloid® 72FP (neutral micronized synthetic amorphous silica gel commercialized by Grace, 103 mg) was taken up in a mixture of 2.0 mL water and 1.0 mL acetonitrile/water (volume ratio 1:1) to obtain a suspension. Amorphous elagolix (100 mg, for example prepared according to the procedure disclosed in WO 2009/062087 A1, example 4B) was dissolved in 2.0 mL acetonitrile/water (volume ratio 1:1) and aqueous sodium hydroxide (50 w %, 1.0 mol equivalent, 8.3 microliter) was added to the solution. The solution was shaken at room temperature and afterwards allowed to stand without shaking for about 10 min, followed by filtration with the aid of a syringe filter (pore size 0.45 microns). Subsequently, the elagolix sodium solution was added to the Syloid® 72FP suspension and the thus obtained mixture was shaken in order to obtain a homogeneous suspension. Finally, the suspension was frozen in a bath of liquid nitrogen and lyophilized at room temperature and a pressure below 2 mbar, yielding an amorphous solid dispersion of elagolix sodium with Syloid® 72FP as a white solid. The corresponding PXRD is depicted in FIG. 1 herein.

Figure 2:
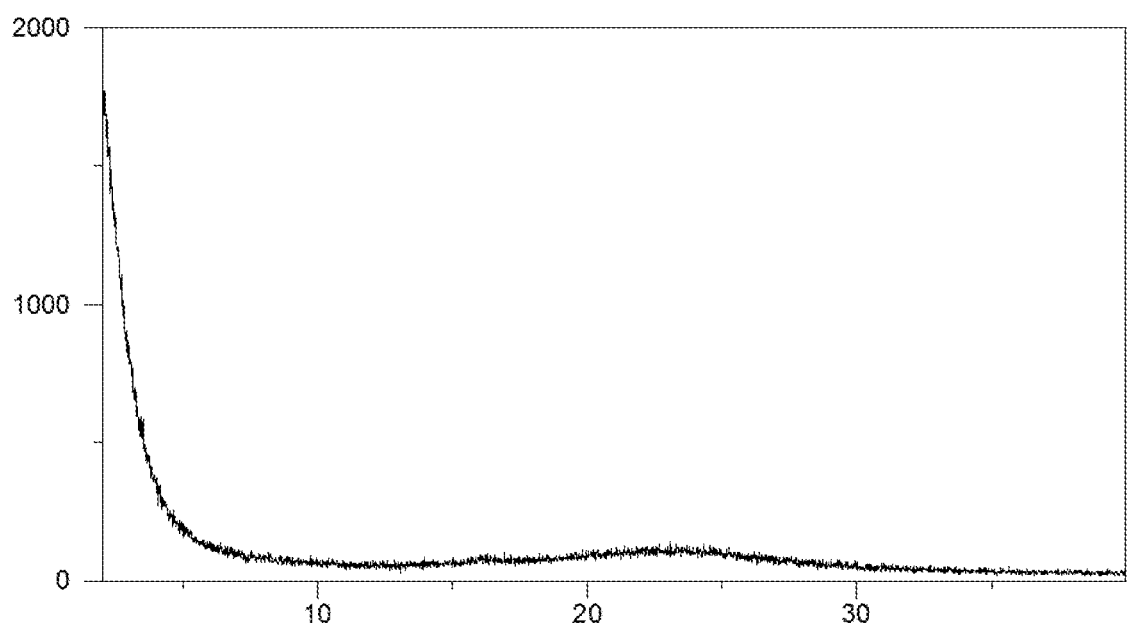
FIG. 2: illustrates a representative powder X-ray diffractogram of the solid dispersion comprising amorphous elagolix sodium and Syloid® AL-1 FP prepared according to Example 1.2 of the present invention. The x-axis shows the scattering angle in °2-Theta, the y-axis shows the intensity of the scattered X-ray beam in counts of detected photons.

Example 1.2: Amorphous Solid Dispersion of Elagolix Sodium With Syloid® AL-1 FP Syloid® AL-1 FP (synthetic amorphous silica commercialized by Grace, 103 mg) was taken up in a mixture of 2.0 mL water and 1.0 mL acetonitrile/water (volume ratio 1:1) to obtain a suspension. Amorphous elagolix (100 mg, for example prepared according to the procedure disclosed in WO 2009/062087 A1, example 4B) was dissolved in 2.0 mL acetonitrile/water (volume ratio 1:1) and aqueous sodium hydroxide (50 w-%, 1.0 mol equivalent, 8.3 microliter) was added to the solution. The solution was shaken at room temperature and afterwards allowed to stand without shaking for about 10 min, followed by filtration with the aid of a syringe filter (pore size 0.45 microns). Subsequently, the elagolix sodium solution was added to the Syloid® AL-1 FP suspension and the thus obtained mixture was shaken in order to obtain a homogeneous suspension. Finally, the suspension was frozen in a bath of liquid nitrogen and lyophilized at room temperature and a pressure below 2 mbar, yielding an amorphous solid dispersion of elagolix sodium with Syloid® AL-1 FP as a white solid. The corresponding PXRD is depicted in FIG. 2 herein.

Example 1.3: Amorphous Solid Dispersion of Elagolix Sodium With Neusilin® UFL2

Figure 3:
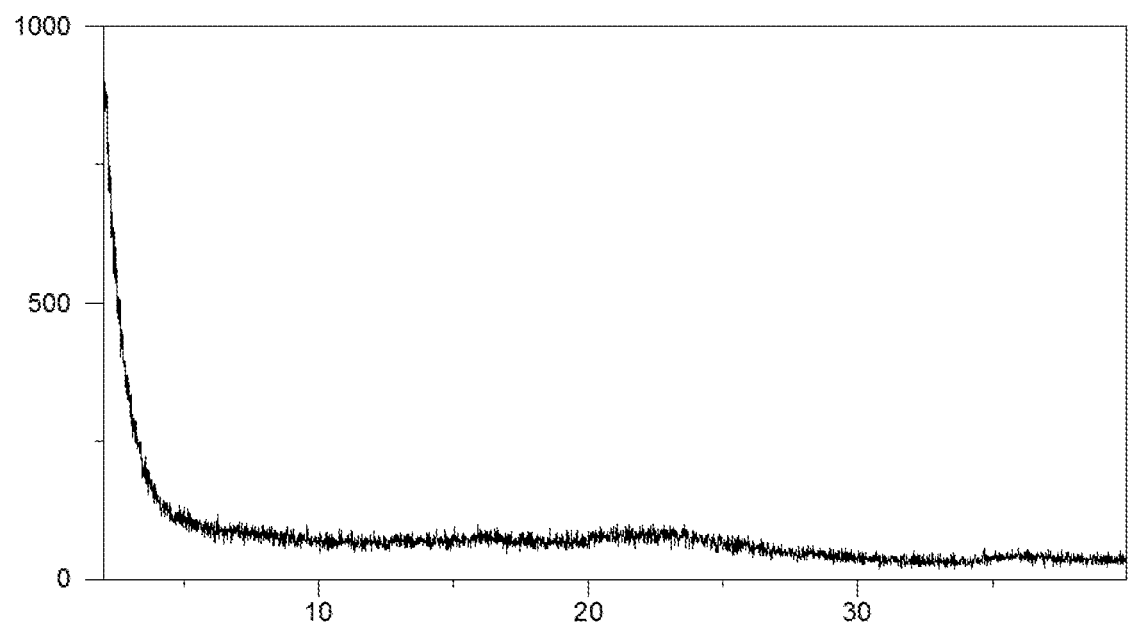
FIG. 3: illustrates a representative powder X-ray diffractogram of the solid dispersion comprising amorphous elagolix sodium and Neusilin® UFL2 prepared according to Example 1.3 of the present invention. The x-axis shows the scattering angle in °2-Theta, the y-axis shows the intensity of the scattered X-ray beam in counts of detected photons.

Neusilin® UFL2 (neutral magnesium aluminometasilicate commercialized by Fuji Chemical Industry Col., Ltd., 102 mg) was taken up in a mixture of 2.0 mL water and 1.0 mL acetonitrile/water (volume ratio 1:1) to obtain a suspension. Amorphous elagolix (100 mg, for example prepared according to the procedure disclosed in WO 2009/062087 A1, example 4B) was dissolved in 2.0 mL acetonitrile/water (volume ratio 1:1) and aqueous sodium hydroxide (50 w-%, 1.0 mol equivalent, 8.3 microliter) was added to the solution. The solution was shaken at room temperature and afterwards allowed to stand without shaking for about 10 min, followed by filtration with the aid of a syringe filter (pore size 0.45 microns). Subsequently, the elagolix sodium solution was added to the Neusilin® UFL2 suspension and the thus obtained mixture was shaken in order to obtain a homogeneous suspension. Finally, the suspension was frozen in a bath of liquid nitrogen and lyophilized at room temperature and a pressure below 2 mbar, yielding an amorphous solid dispersion of elagolix sodium with Neusilin® UFL2 as a white solid. The corresponding PXRD is depicted in FIG. 3 herein.

Example 2: Accelerated Stress Test at 40° C./75% RH With Solid Dispersions Comprising Amorphous Elagolix Sodium and at Least One Silicon-Based Inorganic Compound in a 1:1 Weight Ratio vs. Neat Elagolix Sodium The physical stability against moisture and temperature stress has been tested for different solid dispersions comprising amorphous elagolix sodium and at least one silicon-based inorganic compound and for neat amorphous elagolix. For this purpose, the solid dispersions were stored open at accelerated stress conditions of 40° C. and 75% RH for 1, 3 and 6 weeks respectively. The physical stability has been investigated by means of powder X-ray diffraction and the consistency of the samples was visually controlled. The results are summarized in Table 1 below.

TABLE 1

Result of comparative stress test for different solid dispersions comprising amorphous elagolix sodium and at least one silicon-based inorganic compound and for neat amorphous elagolix sodium

| Silicon-based stabilizer | Initial sample | 1 week at 40° C./75% RH | 3 weeks at 40° C./75% RH | 6 weeks at 40° C./75% RH |
| --- | --- | --- | --- | --- |
| Syloid ® 72FP | amorphous solid | amorphous solid | amorphous solid | amorphous solid |
| Syloid ® AL-1 FP | amorphous solid | amorphous solid | amorphous solid | amorphous solid |
| Neusilin ® UFL2 | amorphous solid | amorphous solid | amorphous solid | amorphous solid |
| elagolix Na | amorphous solid | deliquescence | — | — |

As can be seen from Table 1, the solid dispersions comprising at least one silicon-based inorganic compound of the present invention remained solid throughout the whole stress test. In addition, they did not undergo any solid form transformations e.g. they did not crystallize, which was confirmed by the unchanged powder X-ray diffractograms measured before and after the stress test.

In stark contrast, neat amorphous elagolix sodium deliquesced fairly quickly, when it was subjected to the above described stress conditions. Consequently, the stress test for neat amorphous elagolix was already discontinued at the first check point after one week.

The invention claimed is:

1. A solid dispersion comprising amorphous Elagolix sodium and at least one silicon-based inorganic compound, wherein the silicon-based inorganic compound is a material having a BET specific surface area of at least 1 m$^2$/g, and characterized in that the solid dispersion has a powder X-ray diffractogram comprising no reflection in the range of from 2 to 40° 2-Theta, when measured at a temperature in the range of from 20 to 30° C. with Cu-Kalpha1,2 radiation having a wavelength of 0.15419 nm.

2. The solid dispersion of claim 1, wherein the silicon-based inorganic compound is selected from the group consisting of silica, silicates and combinations of one or more silica with one or more silicate(s).

3. The solid dispersion according to claim 1, wherein the silicon-based inorganic compound has a pH in the range of from 5.0 to 9.0.

4. The solid dispersion according claim 1, wherein the weight ratio of elagolix sodium and the at least one silicon based inorganic compound is in the range of from 1.0:0.1 to 1.0:1.5.

5. The solid dispersion according to claim 1 comprising at least 40 weight-% and at most 95 weight-% of amorphous elagolix sodium, based on the combined weight of the amorphous elagolix sodium and the at least one silicon-based inorganic compound.

6. A pharmaceutical composition comprising the solid dispersion as defined in claim 1 and one or more pharmaceutically acceptable excipient(s).

7. The solid dispersion according to claim 1, wherein the weight ratio of elagolix sodium and the at least one silicon based inorganic compound is in the range of from 1.0:0.2 to 1.0:1.2.

* * * * *